United States Patent [19]

Hart et al.

[11] Patent Number: 4,962,514
[45] Date of Patent: Oct. 9, 1990

[54] METHOD OF CALIBRATING A TOMOGRAPHIC SYSTEM FOR TESTING EARTHEN CORES

[75] Inventors: Timothy J. Hart; Lorne A. Davis, Jr., both of Houston, Tex.

[73] Assignee: Texaco Inc., White Plains, N.Y.

[21] Appl. No.: 273,541

[22] Filed: Nov. 21, 1988

[51] Int. Cl.$^5$ .................. G01N 23/00; G01D 18/00
[52] U.S. Cl. ............................ 378/18; 378/207; 250/252.1
[58] Field of Search ............ 378/18, 22, 207, 156–157; 250/252.1 R, 255

[56] References Cited

U.S. PATENT DOCUMENTS

| | | | |
|---|---|---|---|
| 4,233,507 | 11/1980 | Volz | 378/207 |
| 4,280,047 | 7/1981 | Enos | 250/252.1 |
| 4,323,782 | 4/1982 | Riihimaki et al. | 378/18 |
| 4,527,057 | 7/1985 | Guyton et al. | 378/207 |
| 4,571,491 | 2/1986 | Vinegar et al. | 378/5 |
| 4,599,742 | 7/1986 | Kikuchi et al. | 378/207 |
| 4,613,754 | 9/1986 | Vinegar et al. | 378/207 |
| 4,635,197 | 1/1987 | Vinegar et al. | 378/4 |
| 4,722,095 | 1/1988 | Muegge et al. | 250/252.1 |
| 4,782,502 | 11/1988 | Schulz | 378/207 |
| 4,823,370 | 4/1989 | Kikuchi | 378/7 |

OTHER PUBLICATIONS

SPE 16,952 Computed Tomography as a Core Analysis Tool.

Primary Examiner—Craig E. Church
Assistant Examiner—John C. Freeman
Attorney, Agent, or Firm—Robert A. Kulason; James J. O'Loughlin; Ronald G. Gillespie

[57] ABSTRACT

The present invention concerns a method of calibrating a tomographic system which is used for testing earthen cores. At least two phantoms of a first type of phantom is used in calibrating for contrast resolution. At least two phantoms of a second type of phantom are used to calibrate the tomographic system for beam hardening.

5 Claims, 1 Drawing Sheet

METHOD OF CALIBRATING A TOMOGRAPHIC SYSTEM FOR TESTING EARTHEN CORES

BACKGROUND OF THE INVENTION

1. Field of the Invention

The present invention relates to calibrating tomographic systems for earthen cores.

SUMMARY OF THE INVENTION

The present invention concerns a method of calibrating a tomographic system which is used for testing earthen cores. At two phantoms of a first type of phantom is used in calibrating for contrast resolution, At least two phantoms of a second type of phantom are used to calibrate the tomographic system for beam hardening.

The objects and advantages of the invention will appear more fully hereinafter from a consideration of the detailed description which follows, taken together with the accompanying drawings wherein one embodiment of the invention is illustrated by way of example. It is to be expressly understood, however, that the drawings are for illustration purposes only and are not to be construed as defining the limits of the invention.

DESCRIPTION OF THE INVENTION

Figure 1:
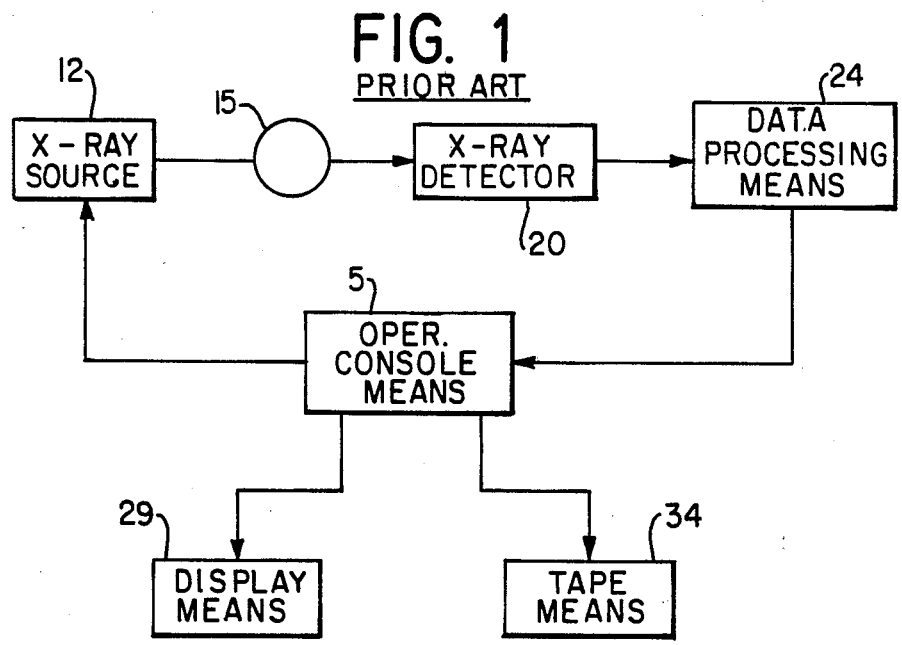
FIG. 1 is a simplified block diagram of a conventional tomographic system which is calibrated in accordance with the present invention.

With reference to FIG. 1, there is shown a conventional type computer tomographic imaging system, hereinafter referred to as the CT, whereby operator console means 5 controls an x-ray source 12 to irradiate a core of earthen material 15 with x-rays. X-rays passing through core 15 are detected by an x-ray detector 20 which provides a signal corresponding to the detected x-rays. The signal corresponding to the detected x-rays is provided to data processing means 24 which in turn provides data to the operator console means 5. Operator console means 5 provides output signals to display means 29 and tape means 34.

Figure 2:
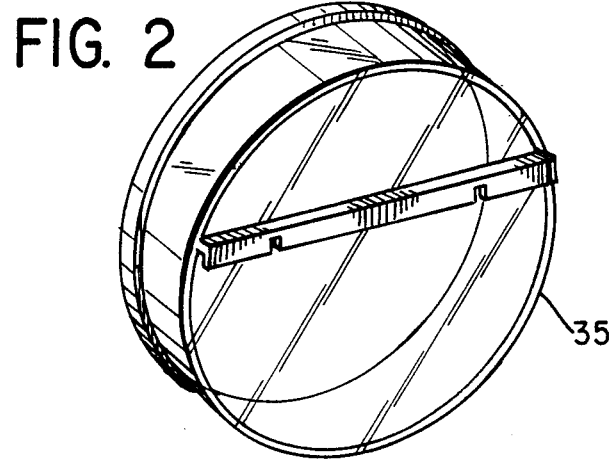
FIG. 2 is an illustration of an A type phantom used in calibrating the system of FIG. 1.

The present invention is a method of calibration which reduces the CT scanner beam hardening artifacts while scanning reservoir cores and rocks. With reference to FIG. 2 there is shown an empty A type phantom 35. A type phantom 35 is used to hold samples of different materials, as hereinafter explained in the beam hardening correction calibration of the tomographic imaging system. Each A type phantom 35 holds a different sample of material. In this method of calibration there are anywhere from two to six phantoms 35 for each material used in calibration. These materials may be but are not limited to, quartz cylinders, Berea sandstone, Indiana limestone, Austin chalk, Carthage marble, and machineable ceramic, hereinafter referred to as Macor. Thus, at least two A type phanton 35 may contain Berea sandstone, at least two other A type phanton 35 may hold Indiana Limestone and so on. These elements are then utilized to determine the standard for the calibrated signals for that particular material. Further, if obtainable, material from an earth formation may also be used.

Figure 3:
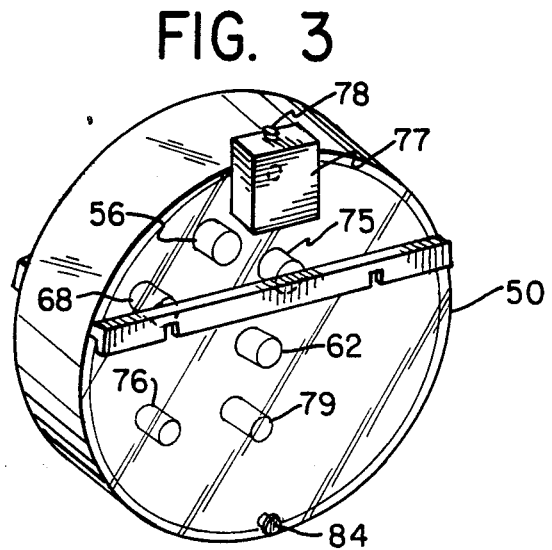
FIG. 3 is a B-type phantom used in calibrating the system of FIG. 1.

The contrast resolution calibration is performed utilizing a B type phantom 50 as shown in FIG. 3. B type phantom 50 constains within it a fused quartz cylinder 56, a Berea sandstone cylinder 62, Indiana limestone cylinder 68, a Macor cylinder 75, Austin chalk boule 76 and a Carthage marble boule 79. B type phantom 50 is hollow on the inside and has a filler tube 77 having a plug 78, a drain plug 84, cylinder 50 is filled with air, with water, or with a high density Freon liquid. Similarly to beam hardening correction calibration, a cylinder of the earthen formation may also be contained in phantom 50.

The system of FIG. 1 is tuned for rocks by scanning A type phantoms 35, each A type phantom 35 has only one material, as previously mentioned. Thus, for a particular material, such as quartz, the plurality of phantoms 35 having quartz allows a reference for quartz to be determined. The data processing means 24 derives standard deviation of the CT readings for quartz. Corrections are made by computer programming until the standar deviation is at its smallest and the image response looks uniform. These steps are repeated for each of the other materials: Berea sandstone, Indiana limestone, Marcor, Austin chalk and Carthage marble.

The contrast resolution calibration requires scanning contrast B type phantoms 50 going from high to low density, i.e. with air in B type phantoms 50, then water and finally a high density Freon liquid. Necessary adjustments to the system area made and the tune-up procedure is repeated. Thus, the contrast between boules 56, 62, 68, 75 76 and 79 and air is provided for in the highest contrast resolution run. The moderate contrast resolution is run with a B type phantom 50 filled with water. A third lower contrast resolution may be run with B type phantom 50 filled with a high density Freon liquid.

To sum up the present invention, it is a method of calibrating a tomographic system for earthen core testing comprising the steps of: calibrating the tomographic system with a plurality of a B type phantom means for contrast resolution, and calibrating the tomographic system with a plurality of an A type phantom means for beam hardening correction. Further the method of the present invention includes providing the B type of phantom means in a manner so as to contain a plurality of different earthen samples in each B type phantom means, while A type phantom means contains only one earthen sample.

In a more restrictive practice of the present invention, the earthen samples in the A type phantom means should be the same material as the earthen samples used in the B type phantom means. The B type phantom means includes a plurality of earthen samples in the phantom means arranged so that there is space in the phantom means between the earthen samples. The contrast resolution calibrating step includes operating the tomographic system in which the medium between the earthen samples within the B type phantom means is air so as to obtain data, operating the tomographic system with the B type phantom means having water as the medium between the earthen samples so as to obtain data, operating the tomographic system in which medium between the earth samples within the B type phantom means is liquid Freon so as to obtain data, and calibrating the tomographic system in accordance with the data accumulated from the operation of the tomographic system with air, water and liquid Freon. Further the beam hardening correction calibrating step includes repeatedly operating the tomographic systems for each A type phantom means to obtain data for each type of earthen material, and determining the beam hardening correction references in accordance with the data obtained in the proceding step.

What is claimed is:

1. A method of calibrating a tomographic system for earthen core testing comprising the steps of:

calibrating the tomographic system with a plurality of a B type phantom means for contrast resolution, and calibrating the tomographic system with a plurality of A type phantom means for beam hardening correction; and in which each A type phantom means contains only one earthen sample, and the contrast resolution calibrating step includes:

providing the phantom means in a manner so that each B type phantom means contains a plurality of different earthen samples, locating the plurality of earthen samples in each B type phantom means so that there is space in the B type phantom means between the earthen samples, operating the tomographic system while the medium between the earthen samples within the B type phantom means is air so as to obtain data, operating the tomographic system with the B type phantom means while having water as the medium between the earthen samples so as to obtain data, operating the tomographic system while the medium between the earth samples within the B type phantom means is liquid Freon so as to obtain data, and calibrating the tomographic system in accordance with the data accumulated from the operation of the tomographic system with each of the B type phantom means containing air, water, and Freon.

2. A method as described in claim 1 in which the beam hardening correction calibration step includes:

providing the plurality of A type phantom means in subgroups, in which the type of earthen samples is different for each subgroup.

3. A method as described in claim 2 in which the plurality of A type phantom means providing step includes:

using earthen samples of one type in each A type phantom means subgroup, corresponding on a one-to-one basis with the plurality of different earthen samples used in each B type phantom means.

4. A method as decribed in claim 2 in which the beam hardening correction calibrating step includes:

repeatedly operating the tomographic systems for each A type phantom means to obtain data for each different type of earthen material, and determining the beam hardening correction references in accordance with the data obtained in the preceding step.

5. A method as described in claim 4 in which the contrast resolution calibrating step includes:

using more than two B type phantoms means, repeatedly operating the tomographic system for each of the more than two B type phantom means to obtain data, and determining the contrast resolution for the tomographic system in accordance with the data obtained in the preceding step.

* * * * *